US00PP25869P3

(12) United States Plant Patent
Dobres

(10) Patent No.: US PP25,869 P3
(45) Date of Patent: Sep. 8, 2015

(54) ***WEIGELA* PLANT NAMED 'NOVAWEIFUS'**

(50) Latin Name: *Weigela hybrida*
Varietal Denomination: Novaweifus

(71) Applicant: CP DELAWARE, INC., Wilmington, DE (US)

(72) Inventor: Michael S. Dobres, Philadelphia, PA (US)

(73) Assignee: CP Delaware, Inc., Wilmington, DE (US)

( * ) Notice: Subject to any disclaimer, the term of this patent is extended or adjusted under 35 U.S.C. 154(b) by 71 days.

(21) Appl. No.: 13/998,891

(22) Filed: Dec. 19, 2013

(65) Prior Publication Data

US 2015/0181789 P1 Jun. 25, 2015

(51) Int. Cl.
*A01H 5/00* (2006.01)

(52) U.S. Cl.
USPC ..... Plt./226

(58) Field of Classification Search
USPC ..... Plt./226
CPC ..... A01H 5/00
See application file for complete search history.

*Primary Examiner* — Kent L Bell

(74) *Attorney, Agent, or Firm* — Buchanan, Ingersoll & Rooney PC

(57) ABSTRACT

The new plant resulted as an induced mutation of the 'Brigela' cultivar (U.S. Plant Pat. No. 12,666). Tissue cultured shoots were subjected to gamma irradiation followed by selection from the resulting plants. A dense compact bushy rounded growth habit is displayed. Attractive light-green somewhat golden foliage having a wavy margin is displayed which resists burning. Attractive red blossoms that contrast well with the foliage coloration are formed commonly from about May to June. The plant is well suited for providing attractive ornamentation in the landscape.

1 Drawing Sheet

Botanical/commercial classification: *Weigela hybrida/ Weigela* Plant.

Varietal denomination: cv. Novaweifus.

SUMMARY OF THE INVENTION

The new plant of the present invention was derived from the 'Brigela' cultivar (U.S. Plant Pat. No. 12,666) through the use of induced mutagenesis followed by selection. More specifically, on Jan. 30, 2007, tissue cultured shoots of 'Brigela' cultivar were subjected to gamma irradiation to form a population of plants which included various mutations. The cultures were rooted, transferred to soil, and were acclimatized during June 2007. The resulting plants were grown and studied in detail for the possible presence of attractive phenotypes during the summer of 2007. A single plant of the present invention was selected and was preserved in view of its unique combination of attractive phenotypic characteristics. Had this plant not been created, identified and preserved it would have been lost to mankind.

It was found that the new *Weigela* plant of the present invention displays the following combination of characteristics:

(a) exhibits a compact bushy rounded growth habit,
(b) forms attractive light-green somewhat golden foliage that resists burning and bears a wavy margin,
(c) forms attractive red blossoms that contrast well with the foliage coloration, and
(d) is well suited for providing attractive ornamentation in the landscape.

During observations to date, the plant has been found to be hardy in U.S.D.A. Hardiness Zone Nos. 5 to 8. Blossoming commonly occurs in abundance from about May to June, and commonly continues to a lesser degree thereafter.

The new cultivar well meets the needs of the horticultural industry and can be grown to advantage as a perennial deciduous shrub to provide ornamentation. For instance, it can be grown in parks, gardens and residential settings.

Plants of the new cultivar can be readily distinguished from other *Weigela hybrida* cultivars including its parent. More specifically, the 'Brigela' parent displays dissimilar variegated foliage and is somewhat less compact.

The new cultivar also can be readily distinguished from the 'Rubidor' *Weigela florida* cultivar (non-patented in the United States). More specifically, the 'Rubidor' cultivar assumes a considerably larger size and lacks the compact growth habit of the new cultivar.

The rooting of softwood stem cuttings has been used to asexually propagate the new cultivar at West Grove, Pa., U.S.A. It has been found that the characteristics of the new cultivar are stable and are reliably transmitted from one generation to another. Accordingly, the new cultivar can be asexually reproduced in a true-to-type manner.

The new cultivar of the present invention has been named 'Novaweifus', and will be marketed under the RUBY FUSION Trademark.

BRIEF DESCRIPTION OF THE PHOTOGRAPH

The accompanying photograph illustrates the new cultivar in color as nearly true as it is reasonably possible make the same in a color illustration of this nature. The plant was approximately five years of age and was being grown outdoors in full sun during August 2011 on its own roots at West Grove, Pa., U.S.A. In view of the lateness in the season, the flower density was less than that displayed earlier in the summer.

DETAILED BOTANICAL DESCRIPTION

The following is a detailed description while observing two-year-old plants of the new cultivar that were produced by the rooting of cuttings. Such plants were being grown in one-gallon containers under greenhouse conditions at West Grove, Pa., U.S.A. The chart used in the identification of color is The R.H.S. Colour Chart (1995 Edition or equivalent) of The Royal Horticultural Society, London, England. Common color terms are to be accorded their customary dictionary significance.

Botanical classification:

*Weigela hybrida*, cv. Novaweifus.

*Parent.*—*Weigela hybrida*, cv. 'Brigela'.

*Plant type.*—Deciduous shrub.

Plant:

*Growth habit.*—Compact bushy rounded.

*Height.*—Approximately 3 to 4 feet on average when mature. This is believed to compare to a height of approximately 4 to 5 feet on average for the 'Brigela' cultivar, and approximately 5 to 6 feet on average for the 'Rubidor' cultivar.

*Spread.*—Approximately 3 to 4 feet on average when mature. This is believed to compare to a width of approximately 4 to 5 feet on average for the 'Brigela' cultivar, and approximately 5 to 6 feet on average for the 'Rubidor' cultivar.

*Stem length.*—Commonly approximately 21.5 cm on average.

*Stem diameter.*—Commonly approximately 3 mm on average.

*Stem aspect.*—Commonly approximately 45 degrees.

*Stem color.*—On new growth near Yellow-Green Group 144A overlaid with Red-Purple Group 78C, and on mature wood near Greyed-Orange Group 177C.

*Stem texture.*—New growth tends to be covered with short pubescence and mature wood is somewhat rough.

*Internode length.*—Commonly approximately 2.5 cm.

*Roots.*—Coarsely fibrous and moderately dense.

Foliage:

*Arrangement.*—Opposite.

*Shape.*—Generally elliptic.

*Apex.*—Cuspidate.

*Base.*—Cuneate.

*Length.*—Commonly approximately 6.5 cm on average.

*Width.*—Commonly approximately 2.5 cm on average.

*Texture.*—On the upper surface glabrous, and on the under surface covered with short pubescence.

*Color.*—On the upper and under surfaces of newly opened leaves near Yellow-Green Group 145A, and on the upper and under surfaces of mature leaves near Yellow-Green Group 144A.

*Margins.*—Entire and wavy.

*Venation.*—Commonly near Yellow-Green Group 145B in coloration on the upper and under surfaces.

*Fragrance.*—None noticeable.

*Petiole.*—Commonly approximately 3 mm in length on average, approximately 2 mm in diameter on average, finely pubescent, and near Yellow-Green Group 145B in coloration.

Inflorescence:

*Season.*—Most abundantly in about May to June.

*Buds.*—Elongated ovoid, 5-lobed, approximately 1.5 cm in length just before opening, approximately 7 mm in diameter, and near Red-Purple Group 60A in coloration.

*Quantity.*—Commonly approximately 2 to 8 flowers arranged in a cyme, terminal or axillary, persistent.

*Flower diameter.*—Approximately 2 cm on average.

*Flower length.*—Approximately 1.5 mm on average.

*Flower configuration.*—Funnel-formed campanulate with petals fused at the base to slightly overlapping.

*Petal number.*—Five.

*Petal shape.*—Reniform.

*Petal apex.*—Rounded.

*Petal margin.*—Entire.

*Petal length.*—Commonly approximately 8 mm on average.

*Petal width.*—Commonly approximately 1 cm on average at the widest point.

*Petal texture.*—Glabrous.

*Petal color.*—When opening: the inner surface is near Red-Purple Group 59D, and the outer surface is near Red-Purple Group 58A. When mature: the inner surface is near Red-Purple Group 64C, and the outer surface is near Red-Purple Group 63A.

*Sepal number.*—Five.

*Sepal shape.*—Lanceolate.

*Sepal length.*—Approximately 5 mm on average.

*Sepal width.*—Approximately 1.5 mm on average.

*Sepal apex.*—Pointed.

*Sepal base.*—Truncate and fused.

*Sepal margin.*—Entire.

*Sepal texture.*—Smooth.

*Sepal color.*—Near Yellow-Green Group 145A on the upper surface, and near Yellow-Green Group 145B on the under surface.

*Stamen number.*—Five.

*Anther shape.*—Basifixed and narrowly oblong in shape.

*Anther length.*—Approximately 4 mm on average.

*Anther color.*—Near Yellow-White Group 158C.

*Filaments.*—Commonly approximately 1.5 cm in length on average, and near White Group 155A in coloration.

*Pollen.*—Present in a sparse quantity, and near Yellow-White Group 158A in coloration.

*Pistil number.*—One.

*Style length.*—Approximately 2.3 cm on average.

*Style color.*—Near White Group 155A.

*Stigma shape.*—Bi-lobed, and recurved.

*Stigma color.*—Near White Group 155A.

*Ovary color.*—Near Yellow-Green Group 145B.

*Seeds/fruit.*—No seed or fruit production has been encountered during observations to date.

*Fragrance.*—None detected.

*Flower longevity.*—Approximately 3 to 4 weeks on the plant.

*Peduncle length.*—Approximately 1.2 cm on average.

*Peduncle diameter.*—Approximately 1 mm on average.

*Peduncle texture.*—Smooth.

*Peduncle color.*—Near Yellow-Green Group 145A.

*Pedicels.*—None, sessile to peduncle.

Disease resistance: Typical of the plant type during observations to date.

Plants of the 'Novaweifus' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Weigela* plant having the following combination of characteristics:

(a) exhibits a compact bushy rounded growth habit, (b) forms attractive light-green somewhat golden foliage that resists burning and bears a wavy margin, (c) forms attractive red blossoms that contrast well with the foliage coloration, and (d) is well suited for providing attractive ornamentation in the landscape;

substantially as illustrated and described.

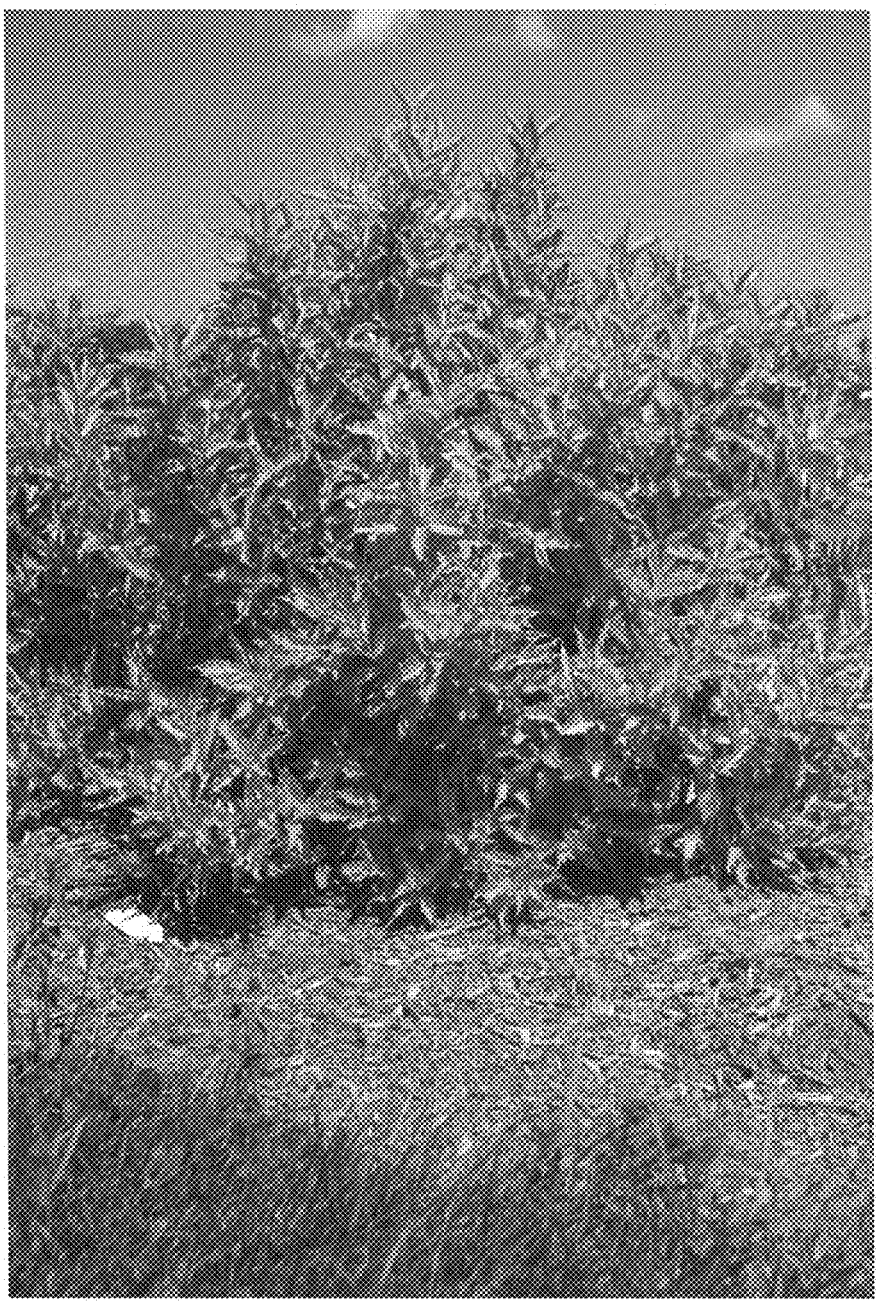

* * * * *